United States Patent [19]

Jullien

[11] Patent Number: 5,188,600
[45] Date of Patent: Feb. 23, 1993

[54] SYRINGE GUARD APPARATUS

[76] Inventor: Robert G. Jullien, 2904 Graham Road, Falls Church, Va. 22042

[21] Appl. No.: 661,242

[22] Filed: Feb. 27, 1991

Related U.S. Application Data

[60] Division of Ser. No. 402,894, Sep. 5, 1989, Pat. No. 5,002,533, which is a continuation-in-part of Ser. No. 360,585, Jun. 2, 1989, Pat. No. 5,015,234.

[51] Int. Cl.⁵ .............................................. A61M 5/00
[52] U.S. Cl. ................................... 604/110; 604/192; 604/198
[58] Field of Search ............... 604/110, 111, 187, 192, 604/198, 263; 206/365, 366

[56] References Cited

U.S. PATENT DOCUMENTS

| | | | |
|---|---|---|---|
| 3,796,359 | 3/1974 | Dick | 604/110 |
| 3,893,608 | 7/1975 | Koenig | 604/110 |
| 4,332,323 | 6/1982 | Reenstierna | 604/110 X |
| 4,447,229 | 5/1984 | Butterfield | 604/111 |
| 4,634,428 | 1/1987 | Cuu | 604/110 |
| 4,728,320 | 3/1988 | Chen | 604/110 |
| 4,770,655 | 9/1988 | Haber et al. | 604/110 |
| 4,801,295 | 1/1989 | Spencer | 604/198 |

Primary Examiner—John D. Yasko

[57] ABSTRACT

A guard for encapsulating a needle of a syringe, e.g. for self-administered injections, fits telescopically over the syringe barrel and is slidable relative thereto between an extended position in which the needle is enclosed within the guard and a retracted, preferably locked, position in which the needle is crushed between the syringe barrel and a closed end of the guard. The closed end is preferably formed by an integral end-piece of needle-capture material which the needle partially penetrates prior to collapsing, and may include a plate of needle-impenetrable material.

10 Claims, 2 Drawing Sheets

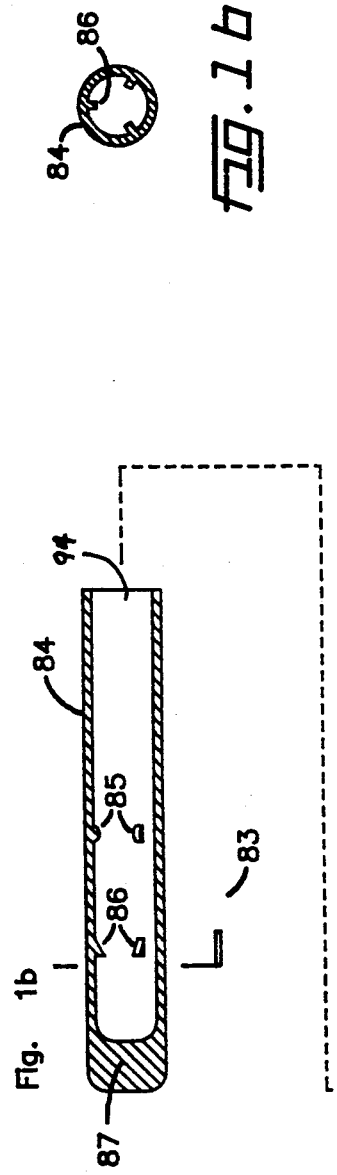
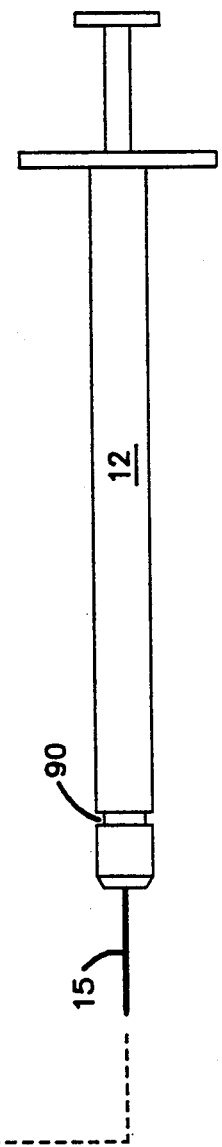
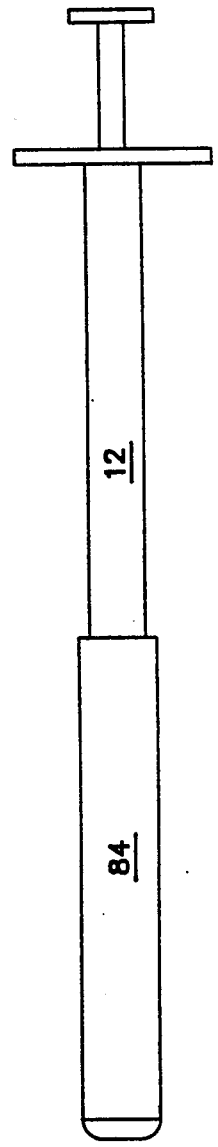

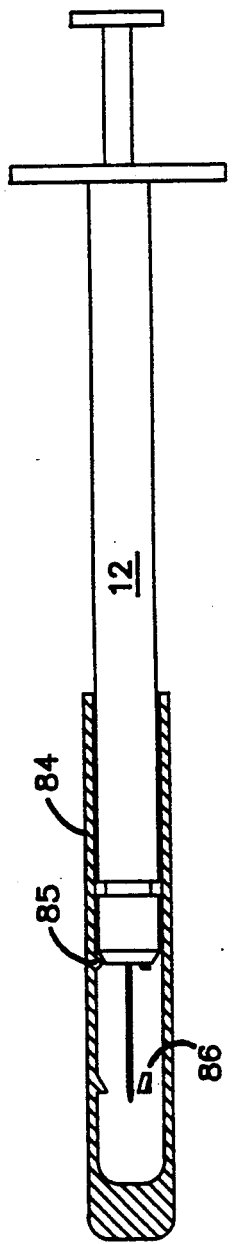
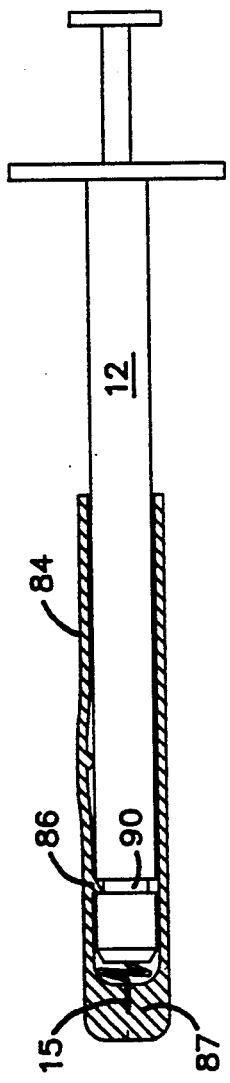
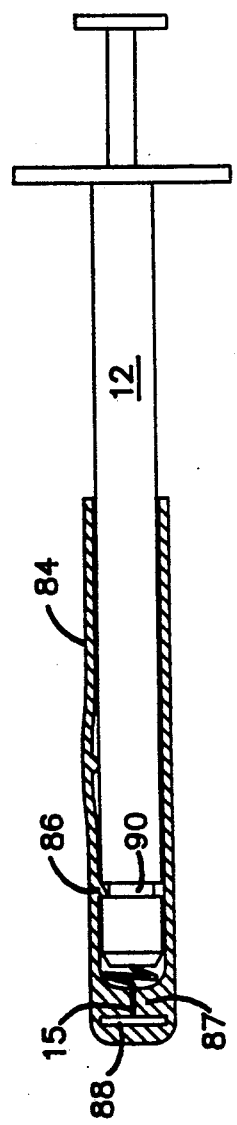

SYRINGE GUARD APPARATUS

PRIOR APPLICATION INFORMATION

This application is a divisional of application Ser. No. 07/402,894 filed Sep. 5, 1989 now U.S. Pat. No. 5,002,533 entitled "Syringe Guard Apparatus", which is a continuation-in-part of application Ser. No. 07/360,585 filed June 2, 1989 now U.S. Pat. No. 5,015,234 entitled "Syringe Apparatus".

FIELD OF THE INVENTION

The present invention relates to the field of medical equipment. Specifically, the present invention relates to an apparatus for preventing unintended contact of a needle, such as a needle of a syringe designed for self-administration of injections, with foreign objects. Particularly, the invention is directed towards the prevention of needle-stick injuries which may occur when an injection is to be or has been given, or a sample been withdrawn, with respect to a patient, and the possible transmission of bloodborne or other fluidborne pathogens as a result of these injuries.

BACKGROUND OF THE INVENTION

Discoveries in medical science have long indicated that certain diseases are passed through unintended contact with contaminated needles. Specifically, blood to blood contact, or internal fluid to internal fluid contact, can spread diseases and pathogens which otherwise cannot be transmitted. To avoid such unintended transmission of pathogens by contaminated needles, particularly for medical professionals, several proposals have been advanced.

The most recent of these proposals has to do with widely available needle, syringe, and needle cap combinations. Specifically, certain governmental agencies are in the process of promulgating guidelines which outline several procedural methods of dealing with the inadvertent spread of infection through contaminated needles. While these procedural suggestions are useful, if they are unobserved, or a participant unavoidably fouls a needle against their person, the disease is none-the-less transmitted.

To address human fallibility with respect to following procedures, several needle guard type apparatuses have been suggested. Specifically, guards which telescopically cover the syringe barrel and needle portion have been proposed. These guards may optionally include latching mechanisms at either end of the guard so as to hold the guard in a particular position with respect to the needle and syringe combination. Further, many of the guards are also proposed as permanent disposal devices for the needle so that if medical waste is improperly disposed of, the risk of a contaminated needle subsequently fouling an individual's person is reduced.

Examples of such prior art guard apparatus can be found in U.S. Pat. Nos. 4,731,059, 4,643,199, 4,425,120, 4,770,655, 4,710,170, 4,728,320, 4,702,738, 4,801,295, and 4,634,428. While these prior art devices provide guards for covering or shielding a needle and syringe combination, they are cumbersome and complex and are therefore not in widespread use.

SUMMARY OF THE INVENTION

It is an object of the present invention to reduce the risk of needle-stick injuries and subsequent disease transmission that may result from these injuries, particularly when using syringes for self-administered injections. The present invention is a simple, two-piece unit and incorporates a syringe and a guard assembly which are telescopically slidable relative to each other between an extended position and a retracted position. In the extended position the syringe needle is safely enclosed within the guard and as the guard and syringe are slid into the retracted position the syringe needle is destructively crushed between the end of the syringe barrel and a closed end of the guard. The unit can optionally include a locking device for securing the unit in the retracted position after the needle has been collapsed, allowing the spent syringe to be disposed of safely.

Additional features and advantages of the present invention will become apparent upon reading the following description of preferred embodiments, taken in conjunction with the accompanying drawings.

BRIEF DESCRIPTION OF THE DRAWINGS

FIG. 1(a) is an exploded part-sectional view of a preferred embodiment of the invention;

FIG. 1(b) is a cross-sectional view on arrows Ib of FIG. 1(a);

FIG. 1(c) is a side elevational view of the embodiment in the extended position;

FIG. 1(d) is a part-sectional view of FIG. 1(c);

FIG. 1(e) is a part-sectional view of the embodiment in the retracted position, after collapse of the syringe needle;

FIG. 1(f) is a part-sectional view of an alternative embodiment of the invention.

DETAILED DESCRIPTION OF PREFERRED EMBODIMENTS

Referring to FIG. 1(a), the assembly comprises a guard 84 in combination with syringe barrel 12 which carries a needle 15 at one end. The syringe barrel 12 is telescopically received within the guard 84, via an open end 94 thereof. The opposite end of the guard 84 is closed, preferably by an integral end-piece of needle-capture material 87.

The preferred assembly includes wedge-shaped protrusions 86 on the inner wall of the guard 84, which engage an annular recess 90 on the syringe barrel 12 as the barrel 12 and guard 84 are slid from the extended position shown in FIGS. 1(c) and (d) into the retracted position, as shown in FIG. 1(e). The end-piece of needle capture material 87 is partially penetrated by the needle 15 as it is crushed upon forcing the assembly into the retracted position, as shown in FIG. 1(e).

To assist positioning of the syringe barrel 12 in the guard 84, tabs 85 are provided on the inner surface of the guard 84 proximal the open end 94 thereof. These tabs 85 contact the outer surface of the syringe barrel 12 as it is slid within the guard 84, which causes the guard 84 to deform by a small amount, as illustrated diagrammatically in FIG. 1(e). The tabs 85 also locate the syringe barrel 12 in the extended, "as-packaged" position, as shown in FIG. 1(d), in which the needle 15 of the syringe is safely enclosed within the guard, until ready for use.

Prior to disposal of the syringe, the guard 84 and syringe barrel 12 with needle 15 are telescoped together and forced into the retracted position by placing the closed end of the guard 84 perpendicular to and against a rigid surface and pushing the syringe barrel 12 telescopically into the guard 84. Needle 15 partially penetrates needle capture material 87 before collapsing. In the final, retracted condition locking wedges 86 lock the syringe guard combination in that retracted position, thereby encapsulating the contaminated needle and sealing the unit for safe disposal.

In the alternative embodiment shown in FIG. 1(f), a plate 88 of needle-impenetrable material is incorporated into the end-piece 87 of the guard 84.

What is claimed is:

1. An assembly for injecting fluid into or drawing fluid from a substrate, said assembly comprising:
   a barrel adapted to contain said fluid and having a needle mounted thereon for transmitting said fluid between said barrel and said substrate;
   tubular guard means for telescopically receiving said needle and at least a portion of said barrel via a first, open end thereof, said guard means being slidable with respect to said barrel between an extended position in which said first end is proximal said portion of said barrel and a retracted position in which said portion of said barrel is proximal a second, closed end of said guard means; and
   locking means between said guard means and said barrel for locking said guard means and said barrel in said retracted position;
   wherein said needle is destructively crushed between said second end of said guard means and said barrel as said guard means is slid from said extended position and locked in said retracted position.

2. An assembly as in claim 1, wherein said locking means comprises at least one projection provided on said guard means for engaging a recess on said barrel.

3. An assembly for injecting fluid into or drawing fluid from a substrate, said assembly comprising:
   an elongated tubular needle extending along a needle axis, said needle having a proximal end adapted to be mounted on a barrel and a distal tip for penetrating said substrate;
   said barrel extending along said needle axis and adapted to contain said fluid, wherein said needle is adapted to transmit said fluid therethrough between said barrel and said substrate; and
   needle destruction means for crushing said needle, said needle destruction means comprising capture means for acquiring and positionally fixing said tip, said capture means for acquiring and adapted to acquire said tip through penetration and to positionally fix said tip in axial alignment with said needle axis, wherein said tip penetrates but does not pass through said mass;
   wherein said needle destruction means is adapted to be collinearly positioned with respect to said needle axis, said tip is acquired by and positionally fixed in said capture means, and said needle is crushed between said proximal end and said capture means.

4. The assembly according to claim 3, wherein said needle destruction means further comprises movement means for advancing said proximal end relative to said capture means.

5. The assembly according to claim 3, wherein said capture means further comprises substantially needle-impenetrable means for limiting penetration of said tip into said mass, wherein said substantially needle-impenetrable means is positioned to permit said capture means to acquire and positionally fix said tip and to limit penetration of said tip within said capture means.

6. The assembly according to claim 3, wherein said proximal end is substantially permanently mounted on said barrel.

7. The assembly according to claim 3, wherein said proximal end is detachably mounted on said barrel.

8. A method of destructively crushing a needle of an assembly for injecting fluid into or drawing fluid from a substrate, said assembly comprising:
   an elongated tubular needle extending along a needle axis, said needle having a proximal end adapted to be mounted on a barrel and a distal tip for penetrating said substrate;
   said barrel extending along said needle axis and adapted to contain said fluid, wherein said needle is adapted to transmit said fluid therethrough between said barrel and said substrate;
   capture means for acquiring and positionally fixing said tip, said capture means adapted to acquire said tip through penetration and to positionally fix said tip in axial alignment with said needle axis, wherein said tip penetrates but does not pass through said capture means; and
   movement means for causing relative motion between said proximal end and said capture means;
   said method comprising the steps of:
   positioning said capture means collinear with respect to said needle axis and proximate said tip;
   relatively moving said proximal end and said capture means toward one another such that said tip is acquired through penetration and positionally fixed in said capture means in axial alignment with said needle axis; and
   crushing said needle between said proximal end and said capture means by further relatively moving said proximal end and said capture means toward one another.

9. The method according to claim 8, further comprising the step of:
   inserting said assembly into receptacle means for providing a reaction surface against which crushing movement occurs, said receptacle means including a cavity having an opening in opposition to an interior face and through which at least a portion of said assebly is inserted, said face providing said reaction surface.

10. The assembly according to claim 3, wherein said needle destruction means further comprises locking means for locking said capture means with respect to said barrel, said locking means adapted to be engaged at the conclusion of crushing said needle.

* * * * *